United States Patent [19]

Jones et al.

[11] Patent Number: 5,514,640
[45] Date of Patent: May 7, 1996

[54] NON-CRYSTALLIZING C14 QUATERNARY AMMONIUM BIOCIDES

[75] Inventors: Ronald Jones, Norcorss, Ga.; Abraham Seldner, Princeton, N.J.

[73] Assignee: Bio Lab, Inc., Decatur, Ga.

[21] Appl. No.: 308,282

[22] Filed: Sep. 19, 1994

Related U.S. Application Data

[63] Continuation of Ser. No. 38,181, Mar. 15, 1993, abandoned, which is a continuation of Ser. No. 658,745, Feb. 21, 1991, abandoned.

[51] Int. Cl.$^6$ .................................................. A01N 33/12
[52] U.S. Cl. ........................... 504/158; 504/151; 514/642; 514/643
[58] Field of Search .................................. 504/158, 160; 514/642, 643

[56] References Cited

U.S. PATENT DOCUMENTS

| | | | |
|---|---|---|---|
| 3,361,795 | 1/1968 | Wakeman et al. | 260/501.15 |
| 3,807,983 | 4/1974 | Abramitis | 71/66 |
| 3,934,025 | 1/1976 | Swered et al. | 424/298 |
| 4,311,512 | 1/1982 | Schwartz | 71/67 |
| 4,911,919 | 3/1990 | Patel et al. | 424/70 |
| 4,978,685 | 12/1990 | Gannon et al. | 514/642 |

OTHER PUBLICATIONS

Cutler et al., CSMA Proceedings, 53rd Annual Meeting (1966).

*Primary Examiner*—Brian M. Burn
*Attorney, Agent, or Firm*—Woodard, Emhardt, Naughton Moriarty & McNett

[57] ABSTRACT

Disclosed is an aqueous composition containing a quaternary ammonium halide wherein at least 75 weight % of the alkyl groups are $C_{14}$-alkyl groups, a $C_1$ to $C_6$ polyhydric alcohol, and a material selected from the group consisting of a $C_{10}$ to $C_{18}$ primary aliphatic alcohol, an ethoxylated alkyl phenol having the formula R—$C_6H_4(OC_2H_4)_n$OH where R is $C_{7-10}$ alkyl and n is 8–10, an ethoxylated aliphatic alcohol having the formula R—$(CH_2CH_2O)_n$OH wherein R is $C_{8-20}$ alkyl or $C_{8-20}$ alkenyl and n is 4–20, a polypropylene glycol aliphatic ether having the formula $CH_3CHOH(CH_2OCHCH_3)_nCH_2O$—R wherein R is $C_{8-20}$ alkyl or $C_{8-20}$ alkenyl and n is 10–15, urea, a $C_8$ to $C_{14}$ fatty acid, mineral oil, and mixtures thereof.

3 Claims, No Drawings

NON-CRYSTALLIZING C14 QUATERNARY AMMONIUM BIOCIDES

This application is a continuation of application Ser. No. 08/038,181, filed Mar. 15, 1993, (now abandoned), which is a Continuation of application number 07/658,745 filed Feb. 21, 1991 (now abandoned).

The present invention relates to quaternary alkylammonium halides wherein at least 75 weight % of the alkyl groups are $C_{14}$-alkyl groups. In particular the present invention relates to aqueous compositions containing quaternary alkylammonium halides wherein at least 75 weight % of the alkyl groups are $C_{14}$-alkyl groups that are useful as a biocide for swimming pools and cooling waters.

Algae growth in swimming pools is unsightly and a safety hazard to swimmers and usually a result of poor pool maintenance. It can cause slipperiness, odors, cloudy murky water, chloramine formation, chlorine demand, bacterial growth, stubborn stains, and the clogging of filters. Low free available chlorine, high temperatures, sunlight, and certain mineral nutrients allow algae growth. Algae growth can be prevented by maintaining the proper level of free available chlorine, periodic superchlorination, and the regular use of an algicide. Algicides serve as a backup to chlorine primarily as a preventative or corrective measure against algae growth in unbalanced pool water. Quaternary ammonium compounds of which the mixed alkyldimethylbenzyl ammonium type with $C_{12}$–$C_{18}$ alkyl groups, are the most common and widely used algicides.

The main types of algae found in swimming pool water are green floating algae, the most common and easiest to control; mustard algae, characterized by orange, yellow, or mustard-colored spots on the walls and floor of the pool; black algae, a blue-green filamentous algae that appears as black slippery spots; and red algae (pink slime), a bacterium with a pink pigment. Quaternary ammonium compounds are generally algistatic when added to water at 2 ppm, and algicidal at about 5 ppm or more.

The use of alkyldimethylbenzylammonium chloride for the control of algae in swimming pools and cooling towers, and other water systems is well known. The effect of the size of the quaternary molecule on the biocidal activity of the homologous series of alkyldimethylbenzylammonium chlorides is well documented. Data shows that of carbon chain lengths from 8–19, $C_{14}$-lengths exhibited lower necessary concentrations to effect bactericidal activity against *Staphlococcus aureus* and *Salmonella typhosa* and *Pseudomonas aeruginosa*. Additional data shows that the quaternary ammonium halide algicide with higher $C_{14}$ concentrations exhibited lower necessary concentrations to effect inhibition against both Phormidium and mustard algae.

Although $C_{14}$ quaternary ammonium compounds are useful as effective algicides, serious problems may arise in the storage and distribution of product formulations with a high percentage of these compounds. These quaternary ammonium compounds are very soluble in water at temperatures above about 16° C. Unfortunately, they crystallize at temperatures below about 16° C. Accordingly, they precipitate from solution on standing at low temperatures and do not readily redissolve on warming. Addition of low molecular weight alcohols or glycols commonly used helps to increase the solubility at reduced temperatures, but creates an additional problem, particularly since an excessive amount of these alcohols and glycols reduces the flash point of the formulations to a point where a real danger of ignition exists.

Accordingly, the present invention provides an improvement in an aqueous composition comprising a quaternary alkylammonium halide wherein at least 75 weight % of the alkyl groups are $C_{14}$-alkyl groups, the improvement wherein the composition further comprises (a) a $C_1$ to $C_6$ polyhydric alcohol and (b) a material selected from the group consisting of a $C_{10}$ to $C_{18}$ primary aliphatic alcohol, an ethoxylated alkyl phenol having the formula R—$C_6H_4(OC_2H_4)_n$OH where R is $C_{7-10}$ alkyl and n is 8–10, an ethoxylated aliphatic alcohol having the formula R—$(CH_2CH_2O)_n$OH wherein R is $C_{8-20}$ alkyl or $C_{8-20}$ alkenyl and n is 4–20, a polypropylene glycol aliphatic ether having the formula $CH_3CHOH(CH_2OCHCH_3)_nCH_2O$—R wherein R is $C_{8-20}$ alkyl or $C_{8-20}$ alkenyl and n is 10–15, urea, a $C_8$ to $C_{14}$ fatty acid, mineral oil, and mixtures thereof. The composition of the present invention is particularly useful as a biocide in treating water in swimming pools. The present invention also provides a method of improving the solubility of a quaternary alkylammonium halide wherein at least 75 weight % of the alkyl groups are $C_{14}$-alkyl groups in an aqueous composition comprising adding to the composition (a) a $C_1$ to $C_6$ polyhydric alcohol and (b) a material selected from the group consisting of a $C_{10}$ to $C_{18}$ primary aliphatic alcohol, an ethoxylated alkyl phenol having the formula R—$C_6H_4(OC_2H_4)_n$OH where R is $C_{7-10}$ alkyl and n is 8–10, an ethoxylated aliphatic alcohol having the formula R—$(CH_2CH_2O)_n$OH wherein R is $C_{8-20}$ alkyl or $C_{8-20}$ alkenyl and n is 4–20, a polypropylene glycol aliphatic ether having the formula $CH_3CHOH(CH_2OCHCH_3)_nCH_2O$—R wherein R is $C_{8-20}$ alkyl or $C_{8-20}$ alkenyl and n is 10–15, urea, a $C_8$ to $C_{14}$ fatty acid, mineral oil, and mixtures thereof. The present invention also provides an improvement in a method of treating water with an aqueous composition comprising a quaternary alkylammonium halide wherein at least 75 weight % of the alkyl groups are $C_{14}$-alkyl groups, the improvement comprising including in the composition (a) a $C_1$ to $C_6$ polyhydric alcohol and (b) a material selected from the group consisting of a $C_{10}$ to $C_{18}$ primary aliphatic alcohol, an ethoxylated alkyl phenol having the formula R—$C_6H_4(OC_2H_4)_n$OH where R is $C_{7-10}$ alkyl and n is 8–10, an ethoxylated aliphatic alcohol having the formula R—$(CH_2CH_2O)_n$OH wherein R is $C_{8-20}$ alkyl or $C_{8-20}$ alkenyl and n is 4–20, a polypropylene glycol aliphatic ether having the formula $CH_3CHOH(CH_2OCHCH_3)_nCH_2O$—R wherein R is $C_{8-20}$ alkyl or $C_{8-20}$ alkenyl and n is 10–15, urea, a $C_8$ to $C_{14}$ fatty acid, mineral oil, and mixtures thereof.

Exemplary quaternary alkylammonium halides wherein at least 75 weight % of the alkyl groups are $C_{14}$-alkyl groups that are useful in accordance with the present invention are well known, such as disclosed in Cutler et al., *CSMA Proceedings 53rd Annual Meeting* (1966), the disclosure of which is incorporated herein by reference. Quaternary ammonium compounds useful in accordance with the present invention are typically made by reacting a suitable $C_{14}$-substituted tertiary amine, such as $C_{14}$-alkyldimethylamine, $C_{14}$-alkyldiethylamine, $C_{14}$-alkylmethylethylamine, $C_{14}$-alkylmethylpropylamine, $C_{14}$-alkylmethylbutylamine, and $C_{14}$-alkylmethylpentylamine, with an alkyl or aryl halide alkylating agent according to well known procedures, such as disclosed in *Kirk-Othmer Encyclopedia of Chemical Technology*, 3rd Ed. Vol 19, p. 522–530, incorporated herein by reference. Exemplary quaternary ammonium compounds useful in accordance with the present invention include $C_{14}$-alkyldimethylbenzylammonium chloride and $C_{14}$-alkyldimethylethylammonium bromide. Typically, such materials are commercially available as mixtures of $C_{14}$ and other higher alkyl ammonium halides.

$C_1$ to $C_6$ polyhydric alcohols useful in accordance with the present invention are saturated and unsaturated aliphatic hydrocarbons having 6, preferably 2–4, carbon atoms and containing one or more, preferably one or two, hydroxyl groups. Exemplary polyhydric alcohols include methanol, ethanol, isopropanol, n-propanol, isobutanol, n-butanol, ethylene glycol, propylene glycols, butylene glycols, and hexylene glycols. The amount of polyhydric alcohol useful in the composition of the present invention varies depending on the other ingredients used.

Ethoxylated alkyl phenols useful in accordance with the present invention are the well known ethoxylated products of alkyl phenols having the formula $RC_6H_4(OC_2H_4)_nOH$ where R is $C_{7-10}$ alkyl, preferably octyl or nonyl and n is 8–11. Commercially available ethoxylated alkyl phenols include TRITON X-100 (R is octyl, n is 9–10) and TRITON X-101 (R is nonyl, n is 9–10) available from Rhom & Haas, Philadelphia, Pa., IGEPAL CO-630 (R is octyl and n is 9–10) and IGEPAL CO-710 (R is nonyl and n is 10.5) available from Gaf Chemical Corp., Wayne, N.J., and TERGITOL NP-9 (R is nonyl and n is 9) available from Union Carbide Chemicals, Danbury, Conn.

$C_8$ to $C_{14}$ fatty acids useful in accordance with the present invention contain 8–14 carbon atoms. Exemplary fatty acids include caprylic acid, capric acid, lauric acid, myristic acid, and mixtures thereof. Commercially available fatty acids useful in accordance with the present invention include EMERY 650 lauric acid, EMERY 659 capric acid, EMERY 655 myristic acid, and EMERY 657 caprylic acid available from Emery Chemicals, Greenville, S.C.

Ethoxylated aliphatic alcohols are the well known ethoxylation products of aliphatic alcohols having the formula $R(CH_2CH_2O)_nOH$ wherein R is $C_{8-20}$ alkyl or $C_{8-20}$ alkenyl, preferably $C_{12-18}$ alkyl or $C_{12-18}$ alkenyl and n is 4–20. Commercially available ethoxylated aliphatic alcohols include BRIJ 30 (R is lauryl and n is 4), BRIJ 92 (R is oleyl and n is 12) and BRIJ 98 (R is oleyl and n is 20) available from ICI Chemical, Wilmington, Del. and NEODOL 25-12 (R is $C_{12-15}$ and n is 12) available from Shell Chemical, Houston, Tex.

$C_{10-18}$-Primary aliphatic alcohols are high molecular weight saturated and unsaturated primary alcohols derived from natural fats and oils. Commercially available materials include ADOL 62 (stearyl alcohol), ADOL 80 (oleyl alcohol), and ADOL 66 (isostearyl alcohol) available from Sherex Chemicals, Dublin, Ohio.

Polypropyleneglycol-$C_{10-18}$-aliphatic ethers are the reaction products of propylene glycol with aliphatic fatty alcohols having the formula $CH_3CHOH(CH_2OCHCH_3)_nCH_2O$—R wherein R is $C_{8-20}$ alkyl or $C_{8-20}$ alkenyl, preferably $C_{12-20}$ alkyl or $C_{12-18}$ alkenyl and n is 10–15. Examples include polypropyleneglycol (11) stearyl ether (n =11), polypropyleneglycol (15) stearyl ether (n=15), and polypropyleneglycol (10) oleyl ether (n=10). Mineral oil useful in accordance with the present invention is preferably 40–90 Saybolt.

The amount of the quaternary ammonium halide in the composition of the present invention preferably makes up 0.1–50 weight % of the composition, more preferably about 10–50 weight %, depending on the quaternary ammonium compound used. For example, for $C_{14}$alkyldimethylbenzylammonium chloride, the preferred amount is 10–40 weight % of the composition, while for $C_{14}$alkyldimethylethylammonium bromide, the preferred amount is 0.5–10 weight %. Preferably, the amount of polyhydric alcohol makes up 1–50 weight % of the composition of the present invention, more preferably about 1–25 weight %, most preferably about 15–20 weight %. The amount of the secondary material comprises about 1–10 weight % of the composition, more preferably about 3–7 weight %. Water makes up the balance of the composition, and preferably comprises about 10–25 weight % of the composition.

Optional ingredients can also be used in accordance with the present invention as long as they do not significantly detract from the stability and biocidal activity of the composition. Optional ingredients include other quaternary ammonium compounds, dyes, perfumes, and cationic and non-ionic surfactants.

To more completely describe the present invention the following non-limiting examples are provided. In the examples all parts and percentages are by weight unless indicated otherwise.

EXAMPLES 1–6

These examples illustrate reducing the crystallization and redissolving temperatures for a series of formulations prepared in accordance with the present invention. Each formulation is placed in a freezer and monitored for crystal growth as the temperature is reduced inside the freezer. The temperature of the formulation is recorded when the first crystals appear. After samples are completely solid they are removed from the freezer and allowed to redissolve by standing at room temperature without agitation. The temperature at which all crystals in the sample are redissolved is recorded. The composition formulations, crystallization temperature, and redissolving temperatures are summarized in the following tables.

TABLE 1

| Ingredients % | Ex. 1 | Ex. 2 | Ex. 3 | Ex. 4 | Ex. 5 | Ex. 6 | Control |
|---|---|---|---|---|---|---|---|
| Water | 28.0 | 33.0 | 38.0 | 33.0 | 38.0 | 30.0 | 50.0 |
| QAC1[1] | 39.5 | 39.5 | 39.5 | 39.5 | 39.5 | 39.5 | 39.5 |
| Ethanol | — | — | — | — | — | 10.0 | 10.0 |
| $(CH_3)_2$—CHOH | 12.0 | 12.0 | 12.0 | 12.0 | 12.0 | — | — |
| Urea | 5.0 | — | 5.0 | — | 10.0 | 15.0 | — |
| QAC2[2] | 0.5 | 0.5 | 0.5 | 0.5 | 0.5 | 0.5 | 0.5 |
| Propylene Glycol | — | — | 5.0 | 15.0 | — | 5.0 | — |
| Hexylene Glycol | 15.0 | 15.0 | — | — | — | — | — |

[1] Quaternary ammonium compound prepared by reacting a 38.1 parts tertiary amine (alkyl distribution $C_{14}$ = 95%; $C_{12}$ = 3%; $C_{16}$ = 2%, available under the name BARLENE 14S from Lonza, Inc., Fairlawn, NJ) with 19 parts benzyl chloride, and 0.3 parts caustic soda in 27.8 parts water and 14.7 parts 95% ethanol for about 3 hours at about 80–85° C., producing a material comprising 55 weight % guaternary ammonium chloride.
[2] Quaternary ammonium compound prepared by reacting a 35.7 parts tertiary amine (alkyl distribution $C_{14}$ = 95%; $C_{12}$ = 3%; $C_{16}$ = 2%, available under the name BARLENE 14S) with 25 parts ethyl bromide in 25 parts isopropyl alcohol and 24 parts water for about 3 hours at about 80–85° C., producing a material comprising 50 weight % quaternary ammonium bromide.

TABLE 2

|  | Ex. 1 | Ex. 2 | Ex. 3 | Ex. 4 | Ex. 5 | Ex. 6 | Control |
|---|---|---|---|---|---|---|---|
| Crystal. Temp. °F. | 26 | 28 | 30 | 26 | 30 | 28 | 60 |
| Redisol. Temp. °F. | 60 | 65 | 65 | 65 | 65 | 65 | 80 |
| Flash Point °F. | 96 | 98 | 100 | 96 | 105 | 105 | 105 |

EXAMPLE 7-10

The procedure of Examples 1-6 is followed in these examples. The results are reported in the following tables.

TABLE 3

| Ingredients % | Ex. 7 | Ex. 8 | Ex. 9 | Ex. 10 | Ex. 11 | Ex. 12 |
|---|---|---|---|---|---|---|
| QAC1[1] | 39.5 | 39.5 | 39.5 | 39.5 | 39.5 | 39.5 |
| QAC2[1] | 0.5 | 0.5 | 0.5 | 0.5 | 0.5 | 0.5 |
| $(CH_3)_2$—CHOH | 11.5 | 11.5 | 11.5 | 11.5 | 11.5 | 11.5 |
| Oleyl alcohol | 2.25 | 3.0 | 3.0 | — | 2.25 | — |
| Ethoxy-alcohol[2] | 0.75 | — | — | — | 0.75 | — |
| Hexylene Glycol | — | — | 5.0 | — | — | — |
| Propylene Glycol | — | — | — | 13.0 | 13.0 | 13.0 |
| Water | | | | Balance | | |

[1]As in Examples 1-6; except in Ex. 11 and 12, ADMA-14 (branched $C_{14}$ alkyl chain) available from Ethyl Corp., Baton Rouge, LA, is used instead of BARLENE 14S.
[2]R-$(CH_2CH_2O)_2$OH where R is oleyl

TABLE 4

| | Ex. 7 | Ex. 8 | Ex. 9 | Ex. 10 | Ex. 11 | Ex. 12 |
|---|---|---|---|---|---|---|
| Crystal. Temp. °F. | 20 | 20 | 20 | 20 | 20 | 20 |
| Redisol. Temp. °F. | 65 | 65 | 60 | 60 | 50 | 50 |
| Flash Point °F. | 105 | 100 | 105 | 110 | 105 | 105 |

We claimed:

1. A method of improving the solubility and/or redissolution characteristics of aqueous quaternary alkylammonium halide biocidal compositions comprising 0.1-50 weight % of quaternary alkylammonium halide compounds of the formula:

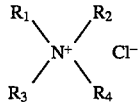

wherein
  $R_1$ and $R_2$ are $C_{1-5}$ alkyl groups;
  $R_3$ is benzyl or ethylbenzyl;
  $R_4$ is selected from the group consisting of $C_{12-18}$ alkyl groups; and
  X is chloride or bromide;
and wherein at least 75 weight % of the $R_4$ alkyl groups are $C_{14}$ alkyl groups; comprising adding to the composition:
  (a) $C_1$ to $C_6$ saturated or unsaturated aliphatic alcohol containing one or more hydroxyl groups;
  (b) a $C_{10}$ to $C_{18}$ primary aliphatic alcohol.

2. A method of improving the solubility and/or redissolution characteristics of aqueous quaternary alkylammonium halide biocidal compositions comprising 0.1-50 weight % of quaternary alkylammonium halide compounds of the formula:

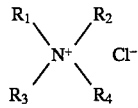

wherein
  $R_1$ and $R_2$ are $C_{1-5}$ alkyl groups;
  $R_3$ is benzyl or ethylbenzyl;
  $R_4$ is selected from the group consisting of $C_{12-18}$ alkyl groups; and
  X is chloride or bromide;
and wherein at least 75 weight % of the $R_4$ alkyl groups are $C_{14}$ alkyl groups; comprising adding to the composition:
  (a) $C_1$ to $C_6$ saturated or unsaturated aliphatic alcohol containing one or more hydroxyl groups;
  (b) a polypropylene glycol aliphatic ether having the formula $CH_3CHOH(CH_2OCHCH_3)_pCH_2O$—$R_5$ wherein $R_5$ is $C_{8-20}$ alkyl or $C_{8-20}$ alkenyl and p is 10-15.

3. A method of improving the solubility and/or redissolution characteristics of aqueous quaternary alkylammonium halide biocidal compositions comprising 0.1-50 weight % of quaternary alkylammonium halide compounds of the formula:

wherein
  $R_1$ and $R_2$ are $C_{1-5}$ alkyl groups;
  $R_3$ is benzyl or ethylbenzyl;
  $R_4$ is selected from the group consisting of $C_{12-18}$ alkyl groups; and
  X is chloride or bromide;
and wherein at least 75 weight % of the $R_4$ alkyl groups are $C_{14}$ alkyl groups; comprising adding to the composition:
  (a) $C_1$ to $C_6$ saturated or unsaturated aliphatic alcohol containing one or more hydroxyl groups;
  (b) a $C_8$ to $C_{14}$ fatty acid, or mixtures thereof.

* * * * *